United States Patent [19]

Granger et al.

[11] Patent Number: 4,752,575
[45] Date of Patent: Jun. 21, 1988

[54] LYMPHOTOXINS WITH ANTITUMOR ACTIVITY AND METHOD FOR PRODUCING SAME

[75] Inventors: Gale A. Granger, S. Laguna; Robert S. Yamamoto, Santa Ana, both of Calif.

[73] Assignee: The Regents of the University of California, Berkeley, Calif.

[21] Appl. No.: 674,588

[22] Filed: Nov. 26, 1984

[51] Int. Cl.$^4$ ............ C12P 21/00; C12N 5/00; A61K 37/02
[52] U.S. Cl. ............................... 435/68; 514/2; 530/351; 435/240.21; 435/240.25
[58] Field of Search ............... 435/68, 240, 241, 948; 424/88, 85; 530/351; 514/2

[56] References Cited

U.S. PATENT DOCUMENTS

| | | | |
|---|---|---|---|
| 4,256,588 | 3/1981 | Hoehm et al. | 210/214 R |
| 4,405,601 | 9/1983 | McEntire et al. | 424/95 |
| 4,411,992 | 10/1983 | Gillis | 435/240 |
| 4,438,032 | 3/1984 | Golde et al. | 435/240 |
| 4,495,282 | 1/1985 | Ohnishi et al. | 424/88 |

OTHER PUBLICATIONS

Kobayashi et al, "Mechanism of Phorbol Myristate Acetate-Induced Lymphotoxin Production by a Human T Cell Hybridoma", Journal of Biochemistry 95, pp. 1775-1782 (1984).
Asada et al, "Human T-Cell Hybridomas Producing Lymphokines, II. Enhancement of Lymphotoxin Secretion by Phorbal Myristate Acetate", Cellular Immunology 77(1), pp. 150-160 (1983).
Johnson et al, "Purification to Electrophoretic Homogeneity of Human Alpha Lymphotoxin from a Cloned Continuous . . . ", Molecular Immunology 20(11), pp. 1241-1244 (1983).
The Merck Index, tenth edition (1983), #7217.
Le et al, "Human T Cell Hybridomas Secreting Immune Interferon", Proceedings of the National Academy of Sciences 79, pp. 7857-7861 (1982).
Le et al, "Synthesis of Alpha and Gamma Interferons by a Human Cutaneous Lymphoma with Helper T-Cell Phenotype", Cellular Immunology 72(1), pp. 157-165 (1982), C.A. 98: 399w.
Devlin et al, "Lymphotoxins: After Fifteen Years of Research", Lymphokines vol. 9, pp. 313-333 (1984).
Harris et al, "Human LT Serum. X. The Initial Form Released by T-Enriched Lymphocytes is 150000 m.w., Associated with Small . . . ", Journal of Immunology 126(6), pp. 2165-2170 (1981).
Kobayashi et al, Journal of Immunology 137(6), pp. 1885-1892 (1986).
Phorbol Myristate Acetate Induction of Lymphotoxins from Continuous Human B. Lymphoid Cell Lines In Vitro, J. Biol. Med., vol. 3, pp. 76-87 (1983).
The Human LT System, Cellular Immunology, 38, 388-402 (1978).
Cytotoxic Activity of Lymphocytes, Journal of Immunology, vol. 116, No. 3, Mar. 1976.

Primary Examiner—John Edward Tarcza

[57] ABSTRACT

Two lymphotoxins are disclosed which are effective in mediating growth of malignant cell lines. The two lymphotoxins are designated as LT-2 and LT-3. A method for producing LT-2 and LT-3 is disclosed in which HUT-102 cells are stimulated with 4 Beta Phorbal 12-Myristate 13-Acetate (PMA).

5 Claims, 3 Drawing Sheets

LYMPHOTOXINS WITH ANTITUMOR ACTIVITY AND METHOD FOR PRODUCING SAME

BACKGROUND OF THE INVENTION

The present invention relates generally to lymphotoxins and lymphoblastoid cell lines useful in production of lymphotoxins. More particularly, the present invention relates to the discovery of two new lymphotoxins which have antitumor activity. The present invention also relates to the production of useful quantities of these two lymphotoxins by stimulation of the HUT-102 continuous human cell line.

The publications and other reference materials referred to herein to describe the background of the invention and to provide additional detail regarding its practice are hereby incorporated by reference. For convenience, the reference materials are numerically referenced and grouped in the appended bibliography.

It is well known that lymphocytes can be stimulated by co-culture with antigens or mitogens in vitro to release a complex family of soluble effector molecules known as lymphokines(1). Lymphotoxins (LT) are a type of lymphokine which are cytotoxic for cells in vitro. Various LT's have been shown to selectively attack neoplastic cells in preference to primary cells in vitro. As a result, much interest has been generated in isolating and studying LT molecules due to their possible use as antitumor agents.

In the past, studies of LT have been difficult because LT forms found in lymphocyte supernatant have been shown to be functionally and physically heterogeneous (2, 3). The past studies have been conducted with unseparated populations of lymphocytes which leads to the heterogeneity of the LT forms found in the supernatant. The various LT forms or molecular weight classes which have been found in lymphocyte supernatant include complex (CX), alpha ($\alpha$), beta ($\beta$) and gamma ($\gamma$). The LT classes are identified and classified by molecular weight (mw) as follows: CX=200,000 daltons (d) or greater; alpha=70,000-90,000 d; beta=30,000-50,000 d and gamma=15,000-25,000 d (2).

The problem regarding heterogeneous LT forms in lymphocyte supernatants has been partially resolved by the finding that different classes of human lymphocytes can be stimulated in vitro to release different and common LT forms (1, 4). Human natural killer cells (NK) stimulated with lectins or contacted with sensitive target cells, release LT forms termed NK-LT that are functionally different from other LT forms for they appear to be species specific, bind and lyse NK sensitive target cells (K-562 and MOLT-4), but do not lyse NK resistant cells (Raji) in vitro (5, 6). Freshly isolated human T cells can be stimulated with lectin to release large MW LT forms such as precursor alpha heavy (140,000-160,000 d) and alpha heavy (140,000-120,000 d) that are unique to T cells. Upon mild denaturation, these forms can be reduced into the smaller molecular weight LT classes (4). Also, continuous human B cell lines appear to release a very restricted MW class of alpha LT with a MW of 90,000-100,000 d.

There is presently a continuing need to isolate and identify new LT's which are useful as antitumor agents and to develop methods for producing supernatants having relatively large, homogeneous amounts of the LT for isolation and use as an antitumor agent.

SUMMARY OF THE INVENTION

In accordance with the present invention, two new LT forms are disclosed which are effective as antitumor agents. A method for producing these new LT forms in useful quantities from a continuous human T cell line is also disclosed.

The present invention is based on the discovery that stimulation of the continuous human T cell line HUT-102 with 4 Beta-phorbal 12-myristate 13-Acetate (PMA) results in the production of two new LT materials which have been shown to have increased antitumor activity over commonly known LT forms. The two LT materials are designated as LT-2 and LT-3. LT-2 and LT-3 are both believed to be proteins having MW's of between 65,000-75,000 d. Both LT-2 and LT-3 were shown to be effective against a battery of different transformed target cells in vitro. However, they had no measureable effect on primary cells under the same conditions and therefore are useful as antitumor agents for selectively attacking tumor cells.

The above discussed and many other features and attendant advantages of the present invention will become better understood by reference to the following detailed description when considered in conjunction with the accompanying drawings.

DETAILED DESCRIPTION OF THE INVENTION

Figure 1:
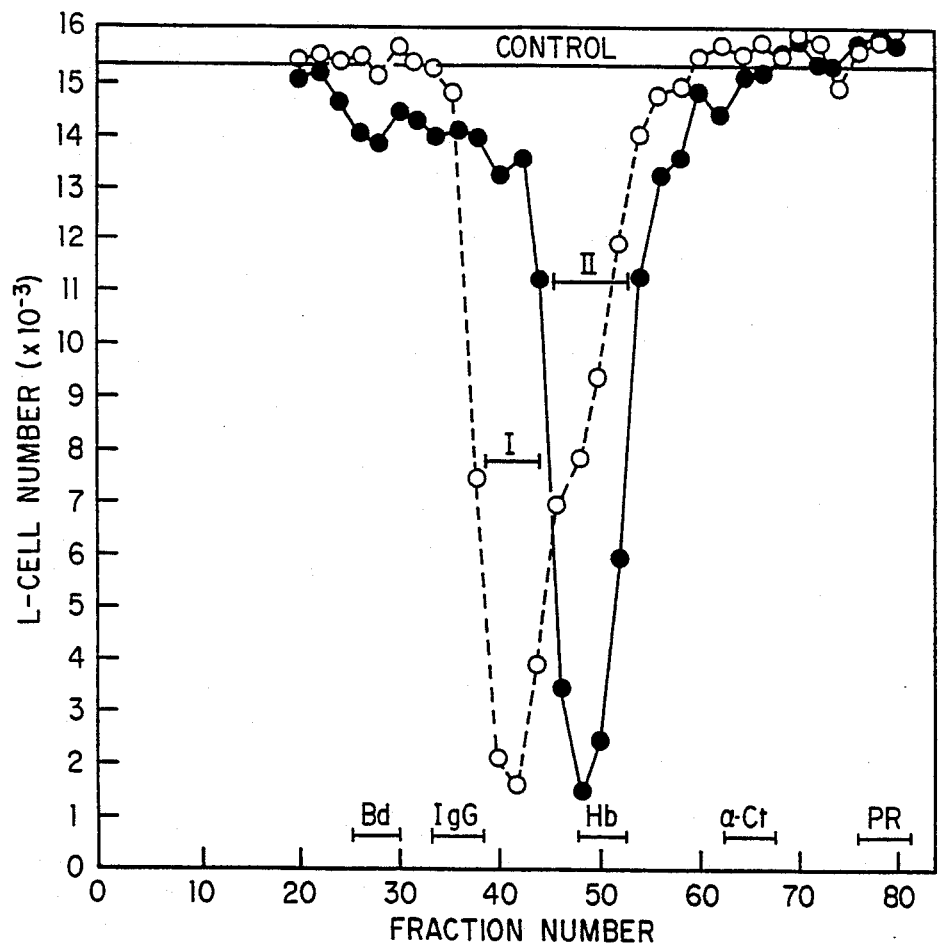
FIG. 1 is the gel filtration chromatography elution profile of the supernatant from PMA stimulated ( ) and non-stimulated (o-o) HUT-102 cells.

HUT-102 is a well known continuous human T cell line which is widely available. The HUT-102 cells used in the following examples were obtained from Dr. Jun Minowada, Roswell Memorial Park, Buffalo, N.Y. HUT-102 cells may also be obtained from Dr. Robert Gallo at the National Institute of Health.

HUT-102 is the preferred cell line for use in obtaining LT-2 and LT-3 in accordance with the present invention. However, it should be noted that other cell lines may be capable of producing LT-2 and LT-3 if properly cultured and stimulated. For example, we have been able to obtain lymphotoxins from cultures of lectin-activated human lymphocytes activated by autologous mixed lymphocyte reaction (AMLR) which have properties and characteristics similar to LT-2. LT-2 type material was also isolated from cloned cytotoxic human T lymphocytes which were stimulated with lectin.

HUT-102 cells are preferred for producing LT-2 and LT-3 due to their ability to produce high levels of lymphotoxins. A comparison of the lymphotoxin production capability of HUT-102 cells with other lymphoid cell lines is set forth in Table 1. The comparison was made for both PMA stimulated and non-PMA stimulated cell lines. PMA is a known tumor promoter which has been shown to exert pleiotropic effects on growth and differentiation processes of cells in a variety of culture systems in vitro (5-8). PMA is known to stimulate and potentiate the production lymphokines in vitro (7, 9).

TABLE 1

Release of Lymphotoxin by PMA and Non-PMA stimulated Continuous Human T Cell Lines in vitro.

| Cell line | Units LT/ml with | |
|---|---|---|
| | PMA | No PMA |
| CCRF-HSB-2 | 6 | 0 |
| HD-Mar 2 | 0 | 0 |
| HPB-ALL | 0 | 0 |
| HPB-MLT | 0 | 0 |
| HUT-78 | 0 | 0 |
| HUT-102 | 332 | 89 |
| JM | 0 | 0 |
| KE-37 | 29 | 0 |
| KOPT-KI | 0 | 0 |
| MOLT-3 | 0 | 0 |
| MOLT-4 | 0 | 0 |
| MT-1 | 0 | 0 |
| Peer | 5 | 0 |
| P30/OKUBO | 2 | 0 |
| RPMI-8402 | 0 | 0 |
| SKW-3 | 5 | 4 |
| TALL-1 | 0 | 0 |
| YT-4E | 124 | 20 |

The various cell lines listed in Table 1, including HUT-102, were obtained from Dr. Jun Minowada and maintained as suspension cultures in RPMI 1640 (Grand Island Biologicals, G.I., N.Y.) supplemented with 10% fetal calf serum (RPMI-FCS) as previously described (10).

The various T cells were grown to a density of $1.5 \times 10^6$ in Corning T-25 cm$^2$ culture flasks (Corning, Corning, N.Y.) in RPMI-FCS. Cells were then transferred into fresh medium at a cell density of $2.5 \times 10^5$ cells/ml and cultured with or without 20 ng/ml 4 Beta Phorbal 12-Myristate 13-Acetate (PMA-Sigma, St. Louis, Mo.) and incubated at 37° C. After 72 hr, supernatants were collected, cleared of cells by centrifugation at $300 \times G$ for 10 min, and the number of units of LT activity determined on murine L-929 cells.

The cell lytic assays summarized in Table 1 were conducted as follows:

All assays were conducted in flat bottomed 96 well microplates with 10-20,000 target cells in 100 ul of medium/well by a modification of the method of Kahn, et al. (11). Adherent cells in microplate wells were stained with crystal violet by the method of Aggarwal et al (12). Nonadherent cells were preincubated with 25 ul of a 1.2 mM solution of the vital dye MTT (Sigma) for 4 hr followed by 10 ul of 25% aqueous solution of gluteraldehyde (Sigma). After 5 min, the microplates are centrifuged at $450 \times G$ for 5 min. and the free dye removed by aspiration. Cells were solubilized by addition of 100 ul of acidified alcohol (40 mM HCl in isopropanol). The amount of stain in each microplate well was then determined by assay in a Flow Titertek Multiskan using a 580 nm filter. The amount of stain in these wells is directly proportional to the number of cells present.

The growth inhibitory lytic (GI-L) effect of a test material is derived by comparison of cell number in test and control wells with all assay performed in duplicate. Two microplate assays for LT which employ murine L-929 target cells were also used; one detects the presence of LT activity, the other measures the amount of LT activity in units/ml in a sample. These arrays are conducted as described above for adherent cells and they have each been described in detail elsewhere (13). A unit of LT activity is that amount of material which lyses 50% of the 20,000 nondividing target cells in 16-20 hrs.

As can be seen from Table 1, the HUT-102 cell line generates substantial amounts of lymphotoxins both spontaneously and with PMA stimulation. Cells from this line were cloned on a monolayer of Balb/C peritoneal macrophages in wells of flat bottomed flow microtiter plates by the limiting dilution method of Levy, et al. (14). Five subclones were isolated by repeated cloning and selection of high level producers. All studies in the present manuscript were conducted with clone YM 1.2. This clone routinely produces from 400-550 units of activity/ml when stimulated with PMA. Large scale culturing of the YM 1.2 cells was accomplished as follows:

YM 1.2 cells were grown to a density of $1.5 \times 10^6$ cells/ml in RPMI-FCS in 3 liter roller bottles. Cells were then washed free of serum by alternate sedimentation at $450 \times G$ for 5 min and resuspended in serum free RPMI. After four washings, cells were resuspended to 1 L in serum free RPMI at a density of $2.5 \times 10^5$ cells/ml. Cell suspensions were then placed in 3 L roller bottles and 20 ng/ml PMA added. After 48-72 hr at 37° C., supernatants were collected and cells removed by sedimentation at $400 \times G$ for 15 min. Supernatants were pooled into 5 L lots, passed through a 0.2 micron filter and concentrated 70 fold by ultrafiltration in an Amicon Stirred Cell with a YM-10 membrane. Concentrates were centrifuged 2 hr at $110,000 \times G$ in a Beckman Model L3-40 Ultracentrifuge, passed through a 0.05 micron filter and stored at $-70°$ C.

YM 1.2 cells were cultured at a density of $2.5 \times 10^5$ cells/ml with 20 ng/ml PMA in serum containing or serum free RPMI. After 24, 48, or 72 hr supernatants were collected, cleared of cells by centrifugation and the number of LT lytic units determined. While the results are not shown, they revealed that PMA induces the release of high levels of cell lytic activity by 24 hr which remains relatively unchanged to 48 hr then declines as much as 30% by 72 hr. The same levels of activity are reached in both serum containing and serum free medium.

Various target cells were established in microplate culture and serial dilutions of a pretested supernatant were then added to each well. After 72 hr, the number of cells remaining in each well was assessed as previously described. The number of units of lytic activity which caused a 50% reduction in target cell numbers was then established. The data shown in Table 2 illustrate that this supernatant has GI-L activity on both human and murine target cells in vitro, including NK sensitive and resistant cells. It is also clear that each transformed cell line expresses its own unique sensitivity to these effectors and this material(s) has no effect on primary non-transformed cells.

TABLE 2

The effect of supernatant from PMA stimulated YM 1.2 cells on various target cells in vitro.

| Cell type | Units of LT causing LD-50 |
|---|---|
| Transformed: Human | |
| Hela | 5 |
| Melanoma | 35 |
| Breast Carcinoma | 56 |
| HT1080 fibrosarcoma | 60 |
| Colon Carcinoma | 75 |
| K-562 | 100 |
| HSB-2(T cell line) | 100 |

TABLE 2-continued

The effect of supernatant from PMA stimulated YM 1.2 cells on various target cells in vitro.

| Cell type | Units of LT causing LD-50 |
|---|---|
| 3104 (B cell line) | 50 |
| Transformed: Murine | |
| Meth A Sarcoma | 300 |
| B16 melanoma | 13 |
| Rift | 12 |
| Non Transformed: Human | |
| WI-38 fibroblasts | No effect detected |
| GM 3468 | No effect detected |
| Non Transformed: Murine | |
| 3T3 fibroblasts | No effect detected |
| Primary fetal cells | No effect detected |

The PMA and non-PMA induced YM 1.2 supernatants were concentrated and subjected to gel filtration chromatography. Shown in FIG. 1 (open circles) is the elution profile of a 48 hr supernatant from non stimulated YM 1.2 cells. As can be seen from FIG. 1 cell lytic activity resolved into one major peak of 80–100,000 MW and a shoulder of activity at 65–70,000 MW. Also shown in FIG. 1 (solid circles) is an elution profile of a 48 hr supernatant from PMA stimulated YM 1.2 cells. There is a single peak of cell lytic activity in the 65–75,000 MW area with little evidence of the 80–100,000 MW material which predominates in the unstimulated supernatant. Similar results were obtained when 24 and 72 hr supernatants were chromatographed on these same columns. Identical results were also obtained when these same fractions were tested on Hela cells, however, the data in FIG. I employed L-929 cells as targets.

Material with a 80–100,000 MW, (peak I), from unstimulated cells and the 65–75,000 MW, (peak II), from stimulated cells was tested on L-929 cells in presence and absence of rabbit anti-alpha LT serum. Production and characterization of rabbit and goat antiserum which specifically neutralize human alpha LT in vitro and the methods to conduct these tests have been previously published (15). The antiserum totally neutralized material from peak I at a ratio of 1 ul serum to 3 units of activity, however, these same sera had no effect on the same level of material from peak II on L-929 cells in vitro. Activity in the peak I appears to be due to the alpha LT form (LT-1), while the activity in peak 2 II is due to two new forms we have named LT-2 and LT-3.

Identification of LT-2 and LT-3 in peak II and purification of each form to homogeneity was conducted as follows.

Figure 2:
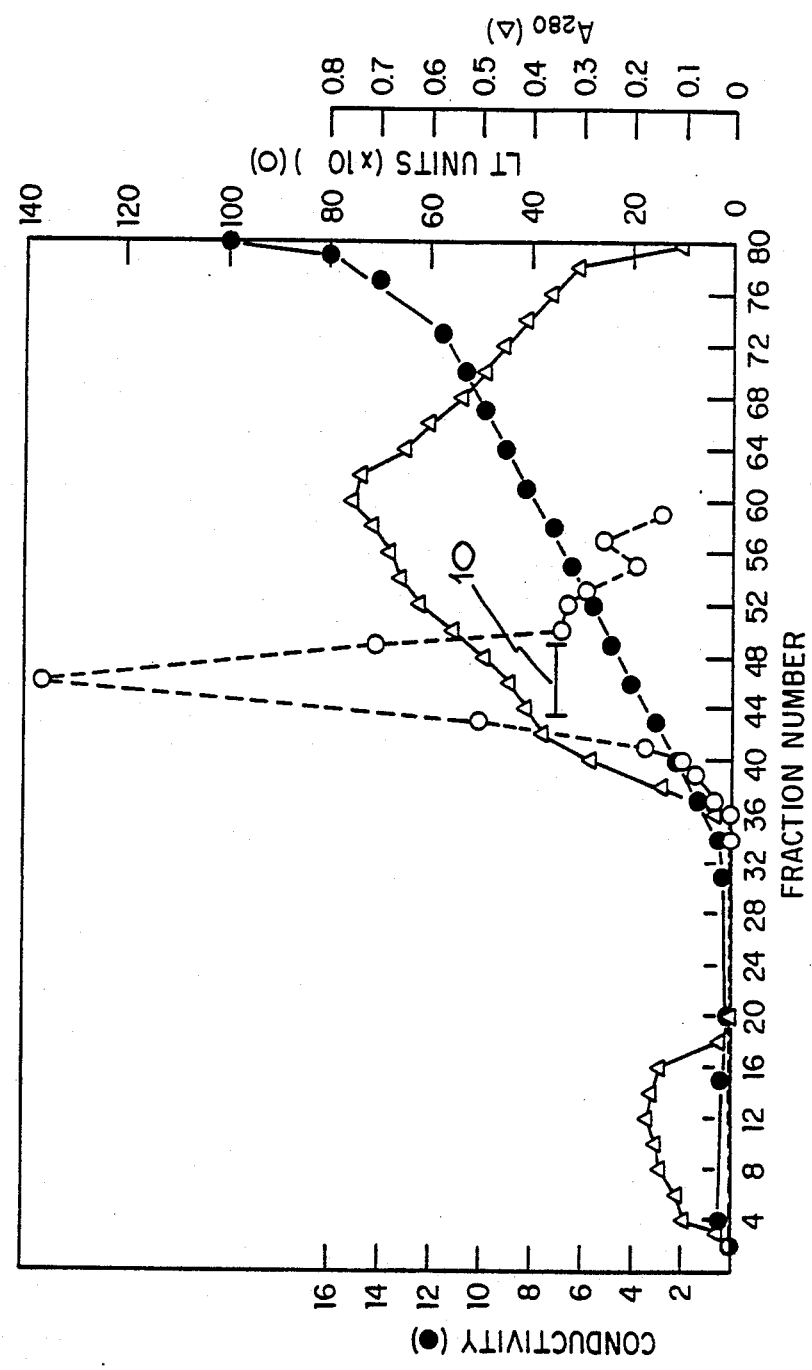
FIG. 2 is the profile of a DEAE column separation of the supernatant from PMA stimulated HUT-102 cells. Cell lytic activity (o-o), protein ( ) and conductivity ( ).

Seventy fold concentrates of 5 L supernatant lots from PMA stimulated YM 1.2 cells were first chromatographed over DEAE columns as follows. Samples were bound to and eluted from 2×10 cm diethylaminoethylcellulose (DEAE) columns with 0.0 to 0.3M Nacl gradients in 0.01M Tris, pH 8.0 at 4° C. as described previously (13). Concentrates of 5.0 L were applied and eluted with a 120 ml gradient into 80 drop fractions at a flow rate of 30 ml/hr. Protein, bioactivity, and conductivity were assessed on each fraction. The profile of one of the DEAE column runs is shown in FIG. 2. Cell lytic activity (open circles) elutes from this column as a single peak of activity.

The fractions containing the major activity were pooled as indicated by the Bar 10 in FIG. 2 and then concentrated to 10 ml by ultrafiltration to form a concentrated pool of LT-2 and LT-3. The total units of activity in the pool sample were determined.

Figure 3:
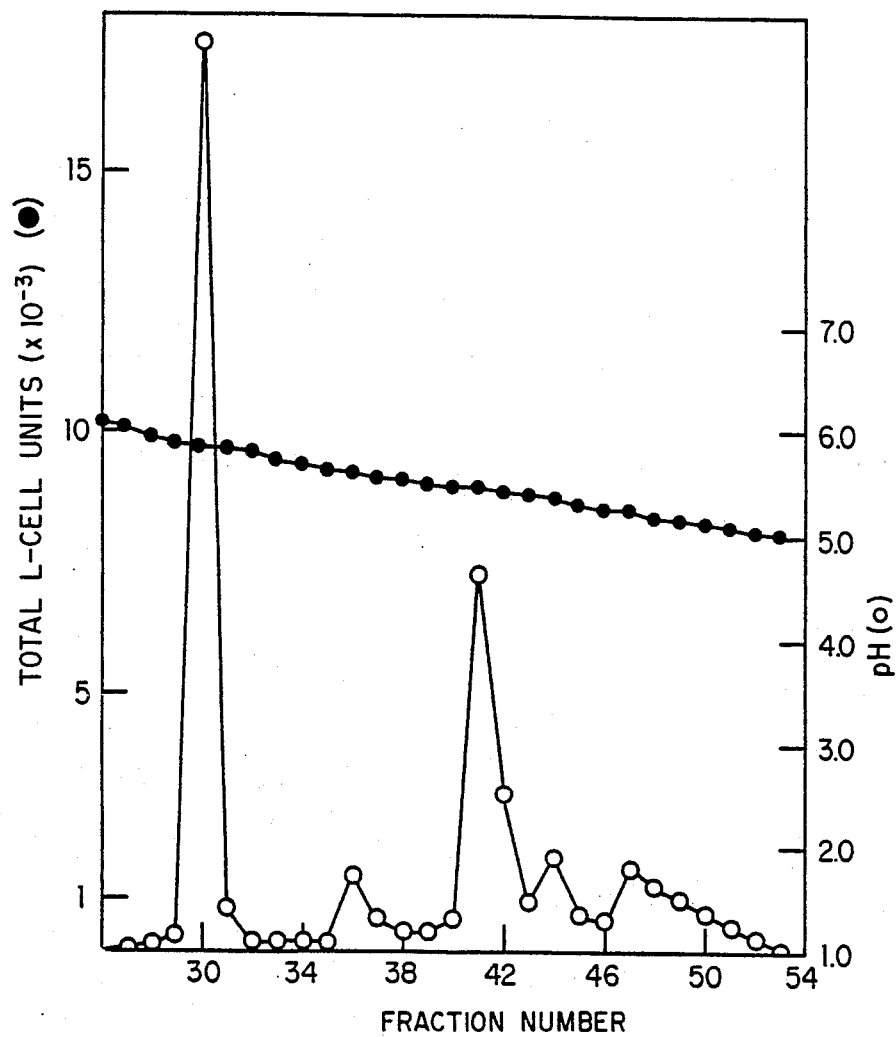
FIG. 3 is a graphical representation of the data from the IEF of the supernatant from PMA stimulated HUT-102 cells. Cell lytic activity (o-o) and PH ( • ı • ).

The pooled LT-2/LT-3 sample was next dialyzed against 100 volumes of 0.01M Tris buffer with three changes every hour for 3 hr and subjected to column isoelectric focusing (IEF) in a 110 ml LKB IEF column in a 4–8 or 5–8 pH gradient in 3% ampholines. Focusing columns were run at 700 volts under constant voltage for 14 hr or until they reached equilibrium and eluted at 20 mls/hr into a fraction volume of 1.8 ml. Individual fractions were assayed for bioactivity and pH as described previously (16). The data from the pH 5–6 region of an IEF column are shown in FIG. 3. Cell lytic activity separates into two major peaks which focus at pH 5.5 (LT-3) and pH 5.8 (LT-2). In certain supernatant lots, a small peak is often seen at pH 6.3. While the data are not shown, we found anti-alpha serum had no effect on LT-3 material, but occasionally gave partial neutralization of LT-2 material and totally neutralized the material at pH 6.3.

One hundred ul of the material from each major peak in FIG. 3 was subjected to electrophoresis in PAGE tube gels. The discontinuous system of Davis (17) was employed. Samples were run in 0.1×20×20 cm slab gels each overlaid with a 1.0 to 1.5 cm stacking gel. Samples were loaded, gels run, and either stained or sliced, and bioactivity eluted from the slices as described previously (13). The rf values for stained or bioactive materials in these gels was based on the relationship of the material to the migration of a bromphenol blue marker. Each eluate was tested for units of cell lytic activity. The LT-3 (pH 5.5) material migrates as a single sharp symmetrical peak with an rf of 0.41 whereas the LT-2 (pH 5.8) material migrates as a single sharp peak with an rf of 0.38.

Samples were then rerun on native PAGE slab gels, the gel was cut in half along the axis of migration, one half silver stained and the other half cut into 1.0 mm slices, and the slices eluted and the eluates tested for bioactivity. Silver stained gels showed a single protein band that coincides with bioactivity, thus indicating that LT-2 and LT-3 are protein.

A summary of the results of a complete purification run are shown in Table 3. There is a yield of 4–7% of the starting material and a specific activity of $10 \times 10^6$ and $13 \times 10^6$ units/mg protein for LT-3 (5.5) and LT-2 (5.8) materials respectively. Focused fractions rapidly lose activity, even at −70° C., however, adjusting the pH to 7.0 with 0.01M Tris and addition of 1% BSA or 5% polyethylene glycol stabilizes the bioactivity. In addition, the LT-2 and LT-3 materials from PAGE slab gels are not neutralized by antiserum directed at human LT.

TABLE 3

Purification of LT-2 and LT-3 from PMA stimulated YM 1.2 Cells.

| Sample | Total protein | Total units | Specific activity |
|---|---|---|---|
| (A). Concentrate (65 ml) | 71 mg | $2.4 \times 10^6$ | 33,800 units/mg |
| (B). DEAE Fraction (20 ml) | 5.7 mg | $6.3 \times 10^5$ | 110,526 units/mg |

TABLE 3-continued

| Purification of LT-2 and LT-3 from PMA stimulated YM 1.2 Cells. | | | |
|---|---|---|---|
| Sample | Total protein | Total units | Specific activity |
| (C). IEF Fraction | | | |
| 1. pH 5.5 (LT-3) (2 ml) | 16 ug | $1.1 \times 10^5$ | $1.38 \times 10^6$ units/mg |
| 2. pH 5.8 (2 ml) (LT-2) | 16 ug | $2.2 \times 10^5$ | $2.64 \times 10^6$ units/mg |
| (D). PAGE Electrophoresis | | | |
| 1. pH 5.5 (LT-3) | 5 ug | $.5 \times 10^5$ | $1.0 \times 10^7$ units/mg |
| 2. pH 5.8 (LT-2) | 8 ug | $1.0 \times 10^5$ | $1.3 \times 10^7$ units/mg |

Samples of LT-3 (pH 5.5) and LT-2 (5.8) material eluted from native PAGE gels were subjected to electrophoresis in SDS nonreducing slab gels according to the method of Laemmli (18). The gels were then silver stained by the technique of Merril, et al. (19). The results showed that LT-3 and LT-2 samples appear as single bands of 69,000±1,000 MW and 79,000±2,000 MW respectively in nonreducing gels. Additional studies were conducted to determine if bioactivity migrates with the protein bands detected in these gels. Both (5.5) and (5.8) material from PAGE gels were run in SDS gels, the gels sliced, materials in the slices eluted, and tested for bioactivity as previously described. The results showed that the biological activity recovered from these gels coincides with the stained band of protein.

PAGE samples of LT-3 (pH 5.5) and LT-2 (pH 5.8) material were then subjected to electrophoresis in SDS reducing slab gels and the gels silver stained. The LT-3 material appeared as a single band at 69,000 MW. However, the LT-2 material appeared as two bands one at 42,000 MW and a second at 21,000 MW. Additional reducing gels of the pH 5.8 material revealed that the LT-2 material could be disassociated completely into the smaller 21,000 MW form.

Lymphoid and nonlymphoid cells were established in microplates and exposed to various levels of the purified LT-3 (5.5) and LT-2 (5.8) materials and crude supernatant. Cultures were visually examined every 24 hr up to 72 hr. Individual plates were stained and assayed on the Multiskan after 72 hr as previously described. The results are shown in Table 4. The LT-3 material is GI-L for all cells tested. The LT-2 material did not affect all targets. Both materials lysed L and Hela cells within the first 24 hr, however, the other target cells required an additional 24 to 48 hr before they were affected. Both LT-3 and LT-2 materials lyse NK resistant Hela cells, however, LT-3 was much more effective on the murine Meth A than LT-2.

trypsin (Worthington Biochemicals 3x cryst.) at 37° C. After 8 hr a soybean trypsin inhibitor was added and the number of units remaining in the treated and test samples was then determined on L-929 cells. All activity in the supernatants was destroyed by this treatment.

All activity in the supernatant was also destroyed by heating supernatants to 80° C. for 5 min at pH's above 9 and below 3. However, activity was stable at 70° C. for 30 min. and supernatants and concentrates could be stored at −4° C. or lypholyzed for long periods without any detectable loss of activity.

The pH of supernatants was adjusted to 6, 5, 4, 3, and 2 with 0.01M acetate buffer and to pH 7, 8 and 9 with 0.01M Tris buffer. All incubations were performed at 4° C. After incubation the pH was readjusted to 7.0 with KOH or acetic acid, the samples were dialyzed overnight against phosphate buffered saline [0.01M phosphate pH 7.2 (PBS)], and the number of units determined in test and control samples on L929 cells. As mentioned above, cell activity was destroyed at pH's above 9 and below 3.

As can be seen from the foregoing examples, supernatants from PMA stimulated HUT-102 contain three lyticly active materials. The three materials were not separated on DEAE (the first step of our purification scheme); however, they were resolved into three peaks at pH 5.5 (LT-3), 5.8 (LT-2), and 6.3 (LT-1) in isoelectric focusing (IEF).

Molecular sieving and antibody neutralization studies revealed that the material at pH 6.3 was the 80-90,000 MW alpha LT form (LT-1). Additional studies revealed this material (LT-1) is a minor component in the PMA induced supernatants of HUT-102. Occasionally we detected a small amount of LT-1 in the 5.8 fraction from IEF, however, we found it was separated from the 5.8 material on native PAGE.

The biochemical, immunological, and functional studies show that the pH 5.5 and 5.8 materials are new

TABLE 4

| The effect of purified LT-2 and 3 on various target cells in vitro | | | | | | |
|---|---|---|---|---|---|---|
| | | | | % viable cells remaining after 72 hr: | | |
| | Units: | Target cells: | | Colon | Brest | |
| Preparation: | tested | Hela | Melanoma | Carcinoma | Carcinoma | Meth A |
| (A). Supernatant: | 420 | 5 ± 3 | 5 ± 4 | 15 ± 6 | 15 ± 7 | 45 ± 10 |
| | 42 | 5 ± 3 | 25 ± 6 | 60 ± 5 | 50 ± 3 | 70 ± 7 |
| (B). LT-3: | 140 | 2 ± 1 | 5 ± 1 | 15 ± 7 | 35 ± 6 | 10 ± 1 |
| (pH 5.5) | 14 | 2 ± 2 | 15 ± 3 | 65 ± 3 | 60 ± 3 | 40 ± 3 |
| (C). LT-2: | 700 | 2 ± 1 | 7 ± 1 | 70 ± 5 | 50 ± 3 | 50 ± 2 |
| (pH 5.8) | 70 | 12 ± 4 | 20 ± 5 | 90 ± 2 | 90 ± 5 | 60 ± 4 |

The LT-2 and LT-3 present in the supernatant of stimulated YM 1.2 cells was further characterized as follows:

The amount of protein in serum free supernatant samples was determined to be 10-19 ug/ml. One ml samples were then exposed to 1:100 (wt:wt) ratio of LT forms LT-3 and LT-2 respectively, since they are not affected by anti-alpha serum and are eluted from sieving gels in the 65-75,000 MW range. Purification of both the 5.5 and 5.8 materials from IEF was achieved by electrophoresis in native polyacrylimide gels (PAGE). The LT-3 material has an rf of 0.41 in PAGE and migrates as a 69,000 MW band in nonreducing SDS PAGE, whereas, the LT-3 material has an rf of 0.38 in native PAGE and migrates as a 79,000 MW band in nonreducing SDS PAGE. As set forth in the examples, the LT-2 material readily dissociated into 21,000 MW subunits in reducing SDS PAGE, however, the LT-3 material is unaffected in the same gels. The LT-2 material is an oligomer of smaller subunits whereas the LT-3 material appears to be a single peptide. The specific activity of each of the purified materials when tested on L-929 cells is: LT-3 = $1.0 \times 10^7$ units/mg and LT-2 = $1.2 \times 10^7$ units/mg. The above identifying characteristics show that LT-2 and LT-3 are unique proteins which have not been previously isolated.

As is apparent from the examples regarding lytic activity of LT-2 and LT-3, both the LT-2 and 3 materials are active on many of the cells tested. LT-3 induced lysis of all transformed targets whereas LT-2 was not as active on all of these cell lines. Both materials are also active on transformed cells from other animal species, however, neither LT form had any detectable effect on any of the primary cell lines tested. One unit of the LT-3 was as active as 3–5 units of LT-2 on the targets that were affected by the LT-2 form. It is clear that both LT-2 and 3 forms have GI-L effects on many different cell lines that are quite resistant to the LT-1 or alpha LT form. Depending upon the cell type the LT-2 and LT-3 forms had either rapid or protracted effects. Hela and L-929 cells were affected within 24 hr, however, all other cells employed required longer incubation periods of 3–4 days.

In view of their ability to lyse a wide variety of target cells in vitro without affecting primary cells, the LT-2 and LT-3 materials are expected to be useful as antitumor agents which can be administered to animals (including humans) when combined with a pharmaceutically acceptable carrier.

An antitumor agent in accordance with the present invention can be prepared according to known methods where the LT-2 and/or LT-3 proteins are combined with a pharmaceutically acceptable carrier. Suitable carriers or vehicles and their formulation are described in Remington's *Pharmaceutical Sciences* by E. W. Martin, which is hereby incorporated by reference.

The antitumor agent will contain an effective amount of LT-2 and/or LT-3 together with a suitable amount of carrier in order to be effective in mediating target cell growth within the animal being treated.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

BIBLIOGRAPHY

1. Granger, G. A., R. S. Yamamoto, and J. Klostergaard. In "Lymphokines Research" (ed. L. Lachman) vol. 1, 45–49, 1982.
2. Granger, G. A., R. S. Yamamoto, D. S. Fair, and J. C. Hiserodt. *Cell. Immunol.* 38: 388–402, 1978.
3. Yamamoto, R. S., J. C. Hiserodt, and G. A. Granger. *Cell. Immunol.* 45: 261–275, 1979.
4. Harris, P. C., R. S. Yamamoto, J. Crane, and G. A. Granger. *J. Immunol.* 126: 2165–2170, 1981.
5. Huberman E., Callahan M. F. Induction of terminal differentiation in human promelocytic leukemia cells by tumor-promoting agents. *Proc. Natl. Acad. Sci. USA* 1979; 76: 1293–1297.
6. Nagasawa K., Mak TW. Phorbal esters induce differentiation in human malignant T llymphoblasts. *Proc. Natl. Acad. Sci. USA* 1980; 77: 2964–2968.
7. Adolf G. R., Swetly P. Tumour-promoting phorbol esters inhibit DNA synthesis and enhance virus-induced interferon production on a human lymphoma cell line. *J. Gen. Virol.* 1980; 51: 61–67.
8. Andreotti P. E. Phorbol ester tumor promotor modulation of alloantigen-specific T lymphocyte responses. *J. Immunol.* 1982; 129: 91–96.
9. Farrar J. J., Mitzel S. B., Fuller-Farrar J., Farrar W. L., Hilfiker M. L. Macrophage-independent activation of helper T cells. I. Production of interleukin 2. *J. Immunol.* 1980; 125: 793–798.
10. Yamamoto, R. S., J. C. Hiserodt, and G. A. Granger. *Cell. Immunol.* 45: 261, 1979.
11. Khan, A., D. Weldon, J. Duvall, S. Pichyangkul, N. O. Hill, D. Muntz, R. Lanius, and M. Ground. In "Human Lymphokines" (eds. A. Khan and N. O. Hill). Academic Press, New York, pp. 23–33, 1982.
12. Aggarwal, B. B., B. Moffat, and R. M. Harkins, *J. Biol. Chem.* 259: 686–691, 1984.
13. Granger, G. A., R. S. Yamamoto, D. S. Fair, and J. C. Hiserodt. *Cell. Immunol.* 38: 388–402, 1978.
14. Levey, R., J. Dilley, and L. A. Lampson. *Curr. Top. Microbiol. Immunol.* 81: 164–172, 1978.
15. Yamamoto, R. S., J. C. Hiserodt, J. E. Lewis, C. E. Carmack, and G. A. Granger. *Cell. Immunol.* 38: 403–416, 1978.
16. Klostergaard, J. and G. A. Granger. *Molec. Immunol.* 18: 455–458, 1981.
17. Davis, B. *Ann. N.Y. Acad. Sci.* 121: 404–427, 1964.
18. Laemmli, V. K. *Nature.* 227: 680, 1970.
19. Merril, C. R., D. Goldman, S. A. Sidman, and M. H. Ebert. *Science.* 211: 1437, 1981.

What is claimed is:

1. A method for producing and isolating lymphotoxins LT-2 and LT-3 produced by a human lymphoblastoid cell, said method comprising the step of:
    cultivating as a single cell suspension the HUT-102 cell line in a nutrient medium in the presence of a stimulative effective amount of PMA so that at least one of the lymphotoxins LT-2 or LT-3 is produced and excreted into said nutrient medium;
    separating and isolating at least one of said LT-2 or LT-3 from said nutrient medium.

2. A protein composition which is separated and purified from the supernatant produced by PMA stimulated HUT-102 cells, said protein composition comprising a protein having the identifying characteristics of LT-2.

3. A protein composition which is separated and purified from the supernatant produced by PMA stimulated HUT-102 cells, said protein composition comprising a protein having the identifying characteristics of LT-3.

4. A composition of matter which is useful as an antitumor agent comprising: a protein composition comprising an effective amount of LT-2 in admixture with a suitable pharmaceutical carrier.

5. A composition of matter which is useful as an antitumor agent comprising: an effective amount of LT-3 in admixture with a suitable pharmaceutical carrier.

* * * * *